(12) United States Patent
Pozdeeva et al.

(10) Patent No.: US 10,888,417 B2
(45) Date of Patent: Jan. 12, 2021

(54) IRIS-LENS DIAPHRAGM

(71) Applicant: OBSCHESTVO S ORGANICHENNOI OTVETSTVENNOSTYU PREDPRIYATIE "REPER-NN", Nizhny Novgorod (RU)

(72) Inventors: Nadezhda Aleksandrovna Pozdeeva, Cheboksaryi (RU); Anastasiya Yurevna Zimitskaya, Nizhny Novgorod (RU); Mihail Mihaylovich Jones, Nizhny Novgorod (RU); Nikolaj Petrovich Pashtaev, Cheboksary (RU)

(73) Assignee: OBSCHESTVO S OGRANICHENNOI OTVETSTVENNOSTYU PREDPRIYATIE "REPER-NN", Nizhny Novgorod (RU)

( * ) Notice: Subject to any disclaimer, the term of this patent is extended or adjusted under 35 U.S.C. 154(b) by 93 days.

(21) Appl. No.: 16/095,397

(22) PCT Filed: Apr. 17, 2017

(86) PCT No.: PCT/RU2017/000240
§ 371 (c)(1),
(2) Date: Oct. 22, 2018

(87) PCT Pub. No.: WO2017/184030
PCT Pub. Date: Oct. 26, 2017

(65) Prior Publication Data
US 2019/0133753 A1 May 9, 2019

(30) Foreign Application Priority Data
Apr. 22, 2016 (RU) .................. 2016115971

(51) Int. Cl.
*A61F 2/16* (2006.01)
*A61F 2/14* (2006.01)
*G02C 7/04* (2006.01)

(52) U.S. Cl.
CPC ............... *A61F 2/16* (2013.01); *A61F 2/14* (2013.01); *A61F 2002/169* (2015.04);
(Continued)

(58) Field of Classification Search
CPC ........ A61F 2002/169; A61F 2002/1683; A61F 2002/1686; A61F 9/007; A61F 2002/1696; G02C 7/046
See application file for complete search history.

(56) References Cited

U.S. PATENT DOCUMENTS 7,025,781 B2    4/2006 Kahn et al.
2011/0264210 A1*  10/2011 Basoglu ............ A61F 2/14
                                                 623/6.14

FOREIGN PATENT DOCUMENTS

CN          102090941 B      1/2016
EP           1674049 A1      6/2006
(Continued)

OTHER PUBLICATIONS

European Search Report dated Nov. 27, 2019 issued in respect of European Patent Application EP17786235.
(Continued)

*Primary Examiner* — David H Willse
*Assistant Examiner* — Tiffany P Shipmon
(74) *Attorney, Agent, or Firm* — BCF LLP

(57) ABSTRACT

There is discloses an iris-lens diaphragm made of elastic material in the form of a colored ring. The iris0lens diaphragm comprises peripheral arc-shaped and open-ended support elements for one-point contact that are capable of
(Continued)

bending in the plane of the colored ring, wherein a thickness of support elements exceeds a thickness of the colored ring.

7 Claims, 2 Drawing Sheets

(52) U.S. Cl.
CPC .......... *A61F 2002/1683* (2013.01); *A61F 2002/1689* (2013.01); *A61F 2002/1696* (2015.04); *G02C 7/046* (2013.01)

(56) References Cited

FOREIGN PATENT DOCUMENTS

| RU | 47693 U1 | 9/2005 |
|----|----------|--------|
| RU | 2275174 C2 | 4/2006 |
| RU | 73196 U1 | 5/2008 |
| RU | 2526245 C1 | 8/2014 |
| RU | 2526248 C2 | 8/2014 |
| WO | 0247584 A1 | 6/2002 |

OTHER PUBLICATIONS

Pozdeeva, "Artificial iris-lens diaphragm in reconstructive surgery for aniridia and aphakia", J Cataract Refract Surg. Sep. 2005;31(9):1750-9. 1016/j.jcrs.2005.02.037, received from the EPO alond with the search report.

Pozdeyeva, "New model of artificial iris-lens diaphragm for correction of large iris defects (clinical and functional results of implantation)", Vestn Oftalmol. Nov.-Dec. 2013;129(6):38-42, 44.

Pozdeeva, "A novel model of artificial iris-lens diaphragm for reconstruction of extensive iris defects (experimental rationale)", Vestn Oftalmol. May-Jun. 2013;129(3):48-53.

Pozdeeva, "Artificial iris-lens diaphragm for reconstructive surgery of combined pathology lens and iris", in the Russian Language, Cheboksary branch GU MNTK "Eye Microsurgery" named. Acad. S.N. Fedorov; 1 LLC Enterprise "Reper-NN", Nizhny Novgorod. English machine translation retrieved on Dec. 2, 2019.

Pzdeeva, "Reconstructive Surgery Combined Pathology of Iris and Crystal Based on Artificial Implantation Irid Crystal Diaphragm", Practical Guide for Doctors, Cheboksary 2006, in the Russian Language. Machine translation retrieved on Dec. 2, 2019.

Pozdeyeva, "Artificial iris-lens diaphragm in reconstructive surgery for aniridia and aphakia", J Cataract Refract Surg—vol. 31, Sep. 2005.

International Search Report of PCT/RU2017/000240 dated Sep. 28, 2017.

International Search Report of PCT/RU2017/000241 dated Sep. 28, 2017.

Okasha, "Artificial iris-lens diaphragm in congenital aniridia", 2015, PM Ophthalmology. Part 1. Aniridia, Practical medicine 02 (15) Ophthalmology. Part 1 | Apr. 17, 2015.

Russian Search Report dated Feb. 7, 2017, issued in connection with the related Russian patent application No. 2016115971.

\* cited by examiner

IRIS-LENS DIAPHRAGM

FIELD OF THE TECHNOLOGY

The invention relates to the field of medicine, more particularly to ophthalmology, and more particularly to reconstructive surgery for pathology of the iris pathology or combined pathology of the iris and lens.

BACKGROUND

Combination of eye-lens opacity with severe iris defects up to total aniridia may be the result of congenital pathology or serious eye injury. Impairment or lack of iris diaphragmatic function leads not only to vision acuity reduction, but also to the formation of a serious cosmetic defect, that can interfere with a social adaptation and professional activity of a person. Different models of artificial iris combined with artificial eye-lens or without it are used in the clinical practice. They are implanted into the eye cavity through a small incision using an injector.

Artificial iris or iris-lens diaphragm (ILD) and its' production method are known, patent is RU 2526245, published on 20 Aug. 2014, A61F9/007, A61F2/14. This iris-lens diaphragm consists of optics and haptics, which are one-piece and made of flexible material. Haptics includes a colored ring and support elements, located on the edge of the colored ring. The colored ring has a pattern imitating a netlike radial pattern of a person's fellow eye iris by its form and color. Support elements are arc-shaped open-ended support elements for one-point contact that are capable of bending in the plane of the colored ring. This iris-lens diaphragm according patent RU 2526245 is the closest analogue to the invention.

Experience has proven that in some surgery cases related to the implantation of the Iris-lens diaphragm according patent RU 2526245 in post-operative period support elements bended and moved the iris-lens diaphragm out-of-plane due to their insufficient rigidity. Iris-lens diaphragm production method, according to patent RU 2526245, allows to increase rigidity of support elements only by enlargement of the total haptics thickness or by making the iris-lens diaphragm of more tough material. But it is unacceptable as it leads to impossibility of the iris-lens diaphragm implantation through the small incision using the injector. Disadvantage of the closest analogue is insufficient rigidity of supporting elements for secure retention of the iris-lens diaphragm in the post-operative period.

SUMMARY

The technical result is aimed at providing support elements with the necessary rigidity and suitable for secure retention, keeping the implantation of an iris-lens diaphragm easy.

The technical result is achieved in that an iris-lens diaphragm is proposed which is made of an elastic material in the form of a colored ring comprising peripheral arc-shaped open-ended support elements for one-point contact that are capable of bending in the plane of the colored ring, wherein the thickness of the support elements exceeds the thickness of the colored ring.

Material resilience of support elements may exceed material resilience of the colored ring. Colored ring may include a flange on the edge. Thickness of the colored ring varies from 0.1 to 0.4 mm, and thickness of the support elements is not more than 0.6 mm. The colored ring may include optics depending on clinical case.

BRIEF DESCRIPTION OF THE DRAWINGS

The non-limiting embodiments of the present technology are depicted in the following drawings.

FIGS. 1-4 depict view of exemplary embodiment of an iris-lens diaphragm that is made in the form of a colored ring 1 comprising peripheral arc-shaped open-ended support elements 2 for one-point contact. The colored ring 1 has a pattern (not showed in the FIGS) imitating the person's fellow eye iris by its form and color. There are holes for anchoring 3 (if required) and manipulations with iris-lens diaphragm during surgery at the bottom of support elements 2. Support elements 2 can be bent in a plane of the colored ring 1. Iris-lens diaphragm can include a flange 4 on the edge of the colored ring 1 as shown in FIGS.3 and 4. Flange 4 can be made of the same material as the support elements 2 like in the FIG. 3, or of another material as shown in the FIG.4.

Figure 1:
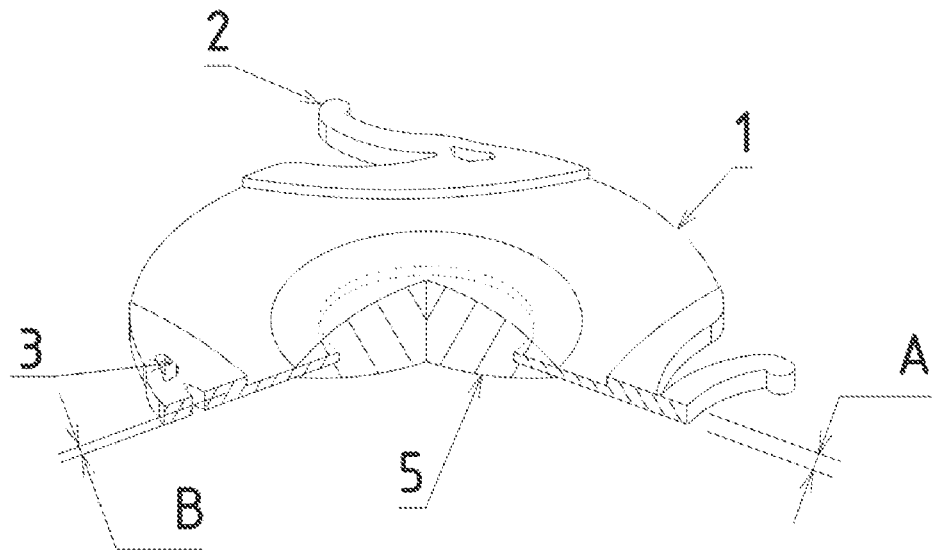
FIGS. 1-4 depict sectional views of exemplary embodiment of an iris-lens diaphragm.

Thickness C of the flanged edge 4 mainly coincides with the thickness A of the support elements 2. Thickness A of the support elements 2 exceeds the thickness B of the colored ring 1, where A is not more 0.6 mm, B—0.1-0.4 mm. The colored ring 1 may include optics 5 depending on clinical case.

DETAILED DESCRIPTION OF THE NON-LIMITING EMBODIMENTS

Figure 2:
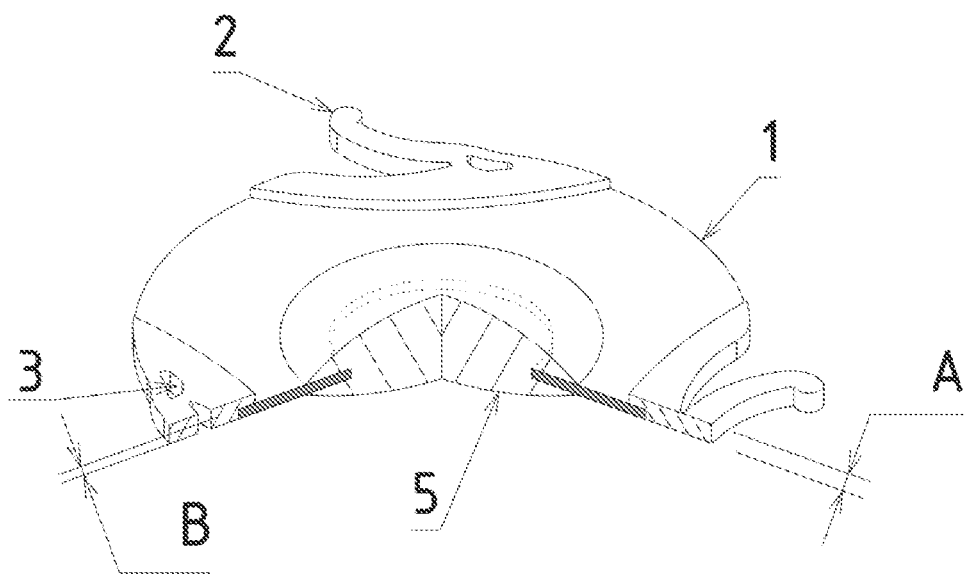
Figure 3:
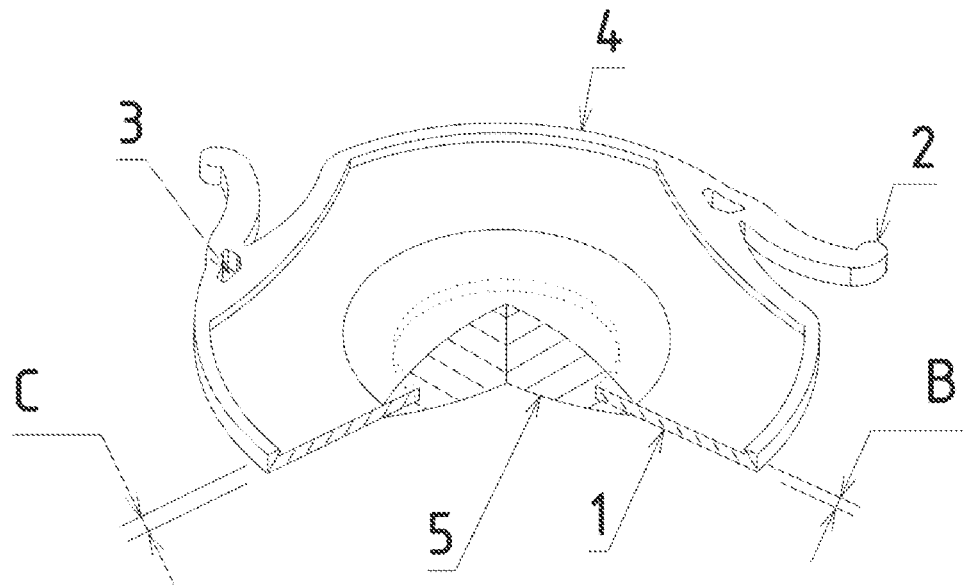
Figure 4:
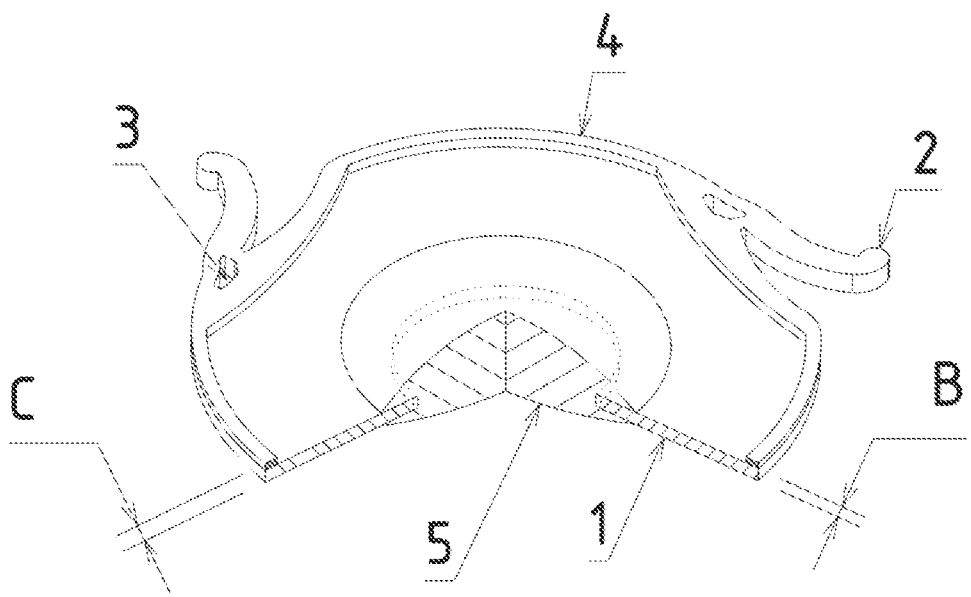

The colored ring 1 and support elements 2 can be made of material with similar (FIG. 1) or different resilience (FIG. 2). In case the colored ring 1 and support elements 2 have different resilience the resilience of support elements 2 exceeds resilience of the colored ring 1. Iris-lens diaphragm by the invention can be manufactured by photo polymerization of the material consisting of methacrylates with different structure: octyl methacrylate, methacrylate with linear hydrocarbon side chain, methacrylate with branched hydrocarbon side chain. Material resilience of iris-lens diaphragm parts varies due to different proportion of the components mentioned above. However, the given example of production method does not limit all possible production methods, which can be different.

Performance of the invention is described below. Iris-lens diaphragm is placed in the ciliary sulcus. Support elements 2 one-point contact against ciliary sulcus and are bent in a plane of the colored ring 1, then fall in line with an individual diameter of the ciliary sulcus, which usually varies from 11.0 mm to 12.5 mm. Support elements 2 make iris-lens diaphragm self-centering. Proposed proportion of material thickness and resilience of support elements 2 and colored ring 1 provides secure iris-lens diaphragm positioning in the ciliary sulcus in post-operative period. In addition, thinner and more flexible colored ring can be easily rolled up to sizes sufficient for injector implantation through the small incision of 2.6 mm for models without optics and up to 3.2-4.0 mm depending on iris-lens diaphragm optical power for models with optics and then it straightens to flat form when leaving the injector. It mitigates the risk of eye injury during the surgery. Flange 4 reduces the load on the thin colored ring 1 from support elements 2 and allows to avoid uncontrolled bends and decentration of the iris-lens diaphragm in post-operative period.

INDUSTRIAL APPLICABILITY

Given below clinical examples depict implantation variants for the invention.

EXAMPLE 1

Patient K. 37 y.o., enquired with clinic complaining of impaired vision, blinding light, sunlight and bright daylight sensitivity after injury of the left pseudophakic eye and subsequent iris prolapse. Diagnosis: OS has a total posttraumatic aniridia, pseudophakia, corneo-scleral corneal cicatrix, mixed astigmatism, state after subtotal vitrectomy in regard to intraocular hemorrhage. Implantation of the described iris-lens diaphragm without optics was proposed to the patient: considering the previously implanted intraocular lens. The iris-lens diaphragm according to the invention was implanted onto the intraocular lens located in the capsular bag, through the corneal tunnel incision of 2.6 mm using the injector. Support elements bumped against ciliary sulcus by their ends and colored ring took a correct central position. Subsequent examinations of the patient in 1, 3, 6, 12 months showed absence of disposition, decentration, sideward bends of the support elements.

EXAMPLE 2

Patient S., 28 y.o., enquired with clinic complaining of monocular diplopia, poor visual acuity, increased sensitivity to glare and serious cosmetic defect of the right eye. In the past medical history, the patient had severe injury of the right eye in adolescence life: there was a partial iris prolapse through the corneo-scleral laceration. The patient got primary surgical treatment and wound was sutured after injury: iris tissue was partially saved, lens mass removed and capsular bag saved. Examination of the right eye showed partial aniridia (absence of iris tissue from 10 to 6 clockwise, aphakia, fibrosis of lens capsule, not critical vitreous degeneration. The following surgical treatment was proposed and performed: implantation of iris-lens diaphragm +19 D through the tunnel incision 3.5 mm long using the injector. Iris-lens diaphragm was implanted onto the surface of lens capsule in the eye; it took central position, resting on the tips of supporting elements at the level of ciliary sulcus. Then discission of lens capsule was performed through the port in the flat area of ciliary body using the vitrectomy cutter. Check-up examinations of the patient in 1, 3, 6, 12 months showed absence of disposition, iris-lens diaphragm decentering, sideward bends of the supporting elements. The patient was satisfied with cosmetic effect, improvement of vision acuity, absence of diplopia and blinding lights.

EXAMPLE 3

Patient T, 46 y.o., enquired with clinic complaining of poor visual acuity in the right eye, embarrassment while daily activity: increased sensitivity to glare, blinding lights, impossibility of being outdoor without sunglasses. In the past clinical history, the patient had radial keratotomy related to high myopia in early years, 2 years ago the patient sustained contusion trauma, as a result there was a laceration of corneal cicatrix and iris prolapse. The patient got primary surgical treatment and corneal cicatrix closure was performed, lens mass removed and capsule partially saved in the upper half. In half a year retinal detachment, which maturated later, was surgically treated with a good anatomic result. At the examination time diagnosis was the following: total post-traumatic aniridia, aphakia with partially saved capsule in the upper half, surgically treated retinal detachment (attached), peripheral and central dry retinal regeneration, corneal cicatrices (after X-ray computer tomography). The following treatment was proposed and then undertaken: Implantation of iris-lens diaphragm (optical power +11 D) into the ciliary sulcus area through the corneo-scleral tunnel 3.5 mm and with transscleral suture fixation in the lower segment through the hole in the bottom of supporting element. In post-operative period iris-lens diaphragm was centered, supporting elements were not displaced and held iris-lens diaphragm in the correct position despite the fact that suturing was performed only in one bottom point. It means that iris-lens diaphragm has sufficient both rigidity and resilience. Follow-up examinations of the patient in 1, 3, 6, 12 months showed absence of disposition, iris-lens diaphragm decentering, sideward bends of the supporting elements. The patient was satisfied with improvement of vision acuity, absence of increased sensitivity to glare.

The invention provides required rigidity and security of supporting elements fixation keeping the ease of iris-lens diaphragm implantation.

The invention claimed is:

1. Iris-lens diaphragm made of elastic material comprising a colored ring having peripheral support elements extending from an edge of the colored ring, the peripheral support elements are adapted for one-point contact and are capable of bending in the plane of the colored ring, wherein the peripheral support elements are arc-shaped and define an open end with a portion of the edge of the colored ring, wherein a thickness of the peripheral support elements exceeds a thickness of the colored ring.

2. Iris-lens diaphragm of claim 1, wherein the colored ring and the peripheral support elements are made of a material with a different resilience, a resilience of the peripheral support elements is more than a resilience of the colored ring.

3. Iris-lens diaphragm of claim 1, wherein the colored ring includes a flange on the edge of the colored ring, a thickness of the flange being equal to the thickness of the peripheral support elements.

4. Iris-lens diaphragm of claim 1, wherein the thickness of the colored ring is from 0.1 mm to 0.4 mm.

5. Iris-lens diaphragm of claim 1, wherein the thickness of the peripheral support elements is not more than 0.6 mm.

6. Iris-lens diaphragm of claim 1, wherein the colored ring includes optics.

7. Iris-lens diaphragm of claim 1, wherein the colored ring and the peripheral support elements are made of a material with a similar resilience.

* * * * *